(12) United States Patent
Fullerton (10) Patent No.: US 11,389,316 B1
(45) Date of Patent: Jul. 19, 2022

(54) COMPRESSION LEG SUPPORT

(71) Applicant: M. J. Fullerton, Pryor, OK (US)

(72) Inventor: M. J. Fullerton, Pryor, OK (US)

( * ) Notice: Subject to any disclaimer, the term of this patent is extended or adjusted under 35 U.S.C. 154(b) by 32 days.

(21) Appl. No.: 15/845,533

(22) Filed: Dec. 18, 2017

Related U.S. Application Data (63) Continuation-in-part of application No. 15/469,064, filed on Mar. 24, 2017, now abandoned, which is a continuation-in-part of application No. 15/186,990, filed on Jun. 20, 2016, now abandoned, which is a continuation-in-part of application No. 14/959,897, filed on Dec. 4, 2015, now abandoned, which is a continuation-in-part of application No. 14/546,191, filed on Nov. 18, 2014, now Pat. No. 9,204,985.

(51) Int. Cl.
*A61F 5/01* (2006.01)
*A43B 7/38* (2006.01)

(52) U.S. Cl.
CPC ............ *A61F 5/012* (2013.01); *A61F 5/0109* (2013.01); *A61F 5/0195* (2013.01); *A43B 7/38* (2013.01); *A61F 5/0113* (2013.01)

(58) Field of Classification Search
CPC .... A61F 5/01–0125; A61F 5/058–0585; A61F 13/04–048; A61H 3/00–04; A61H 9/0078; A61H 9/0085; A61H 9/0092; A61H 5/058; A61H 5/05816; A61H 5/05841; A61H 5/0585; A61H 5/01–0116; A61H 5/012; A61H 5/0127; A61H 5/0195; A61H 5/30–34; A61H 5/02–06; A43B 7/18–20; A43B 7/38; A43B 5/04; A43B 5/07; A43B 13/20
See application file for complete search history.

(56) References Cited

U.S. PATENT DOCUMENTS

| | | | |
|---|---|---|---|
| 1,226,013 A | 5/1917 | Roth | |
| 1,663,921 A | 3/1928 | Pierce | |
| 2,413,053 A | 12/1946 | Kolarik | |
| 2,522,853 A | 9/1950 | Black | |
| 2,558,986 A | 7/1951 | Seelert | |
| 2,632,440 A | 3/1953 | Hauser et al. | |
| 2,943,622 A | 7/1960 | Nelson | |
| 4,372,297 A | 2/1983 | Perlin | |
| 4,494,534 A * | 1/1985 | Hutson | ................ A61F 5/0125 602/16 |

(Continued)

FOREIGN PATENT DOCUMENTS

| KR | 1020060026867 | 3/2006 |
|---|---|---|
| KR | 1020150065943 | 6/2015 |

*Primary Examiner* — Keri J Nelson
*Assistant Examiner* — Michelle J Lee
(74) *Attorney, Agent, or Firm* — Head, Johnson, Kachiglan & Wilkinson, PC (57) ABSTRACT

A leg support that attaches to a user's leg and extends below the user's foot, where stepping on the portion below the user's foot causes the portion around the user's upper leg to tighten. This allows the leg support and the user's leg to bear the user's weight with the user's foot remaining untouched. When the user takes his or her weight off of the leg support, the portion around the user's upper leg loosens for the user's comfort. The leg support insures that there is zero pressure on the bottom of the user's foot and all of the user's weight and vertical shear pressure is converted into horizontal compression pressure around the user's leg.

14 Claims, 7 Drawing Sheets

(56) References Cited

U.S. PATENT DOCUMENTS

| | | |
|---|---|---|
| 4,688,559 A | 8/1987 | Vito et al. |
| 4,848,326 A | 7/1989 | Lonardo |
| 4,865,023 A | 9/1989 | Craythorne et al. |
| 4,953,543 A | 9/1990 | Grim et al. |
| 5,242,378 A | 9/1993 | Baker |
| 5,288,286 A | 2/1994 | Davis et al. |
| 5,490,831 A | 2/1996 | Myers et al. |
| 5,700,237 A | 12/1997 | Hess |
| 6,024,713 A | 2/2000 | Barney |
| 6,960,175 B1 | 11/2005 | Myers |
| 7,393,335 B2 | 7/2008 | Carvey et al. |
| 7,717,869 B2 | 5/2010 | Eischen, Sr. |
| 7,806,842 B2 | 10/2010 | Stevenson et al. |
| 7,815,586 B2 | 10/2010 | Grant et al. |
| 7,918,812 B2 | 4/2011 | Knecht |
| 8,021,316 B2 | 9/2011 | Franke et al. |
| 8,313,448 B2 | 11/2012 | Shimada |
| 8,679,046 B2 | 3/2014 | Ital et al. |
| 2008/0132817 A1 | 6/2008 | Vito |
| 2009/0043234 A1 | 2/2009 | Bledsoe et al. |
| 2009/0227927 A1 | 9/2009 | Frazer |
| 2009/0312683 A1 | 12/2009 | Burns |
| 2010/0106065 A1* | 4/2010 | Ward .................... A61F 5/0104 602/23 |
| 2010/0126514 A1* | 5/2010 | Castellano ............. A43B 3/108 128/845 |
| 2011/0218469 A1 | 9/2011 | Branch et al. |
| 2013/0310719 A1* | 11/2013 | Davis .................. A61H 9/0085 601/149 |
| 2013/0317402 A1 | 11/2013 | Pong et al. |
| 2014/0107549 A1 | 4/2014 | Shih |
| 2017/0189221 A1* | 7/2017 | Fullerton .................. A61F 5/34 |

\* cited by examiner

COMPRESSION LEG SUPPORT

CROSS REFERENCE

This is a continuation-in-part of U.S. patent application Ser. No. 15/469,064 filed Mar. 24, 2017, U.S. patent application Ser. No. 15/186,990 filed Jun. 20, 2016, U.S. patent application Ser. No. 14/959,897 filed Dec. 4, 2015, and U.S. patent application Ser. No. 14/546,191 filed Nov. 18, 2014, now U.S. Pat. No. 9,204,985, which are incorporated herein by reference.

BACKGROUND OF THE INVENTION

Field of the Invention

This invention relates generally to a leg support, and more particularly, but not by way of limitation, to a leg support that allows a user to walk without putting any pressure on the user's foot by transforming a portion of the vertical shear force to horizontal compressive force around the user's upper or lower leg.

Description of the Related Art

There are many circumstances that require a person to keep all pressure off his or her foot or lower leg, including broken bones, sprains, tears, cuts, bruises, abrasions, burns, and injuries due to diabetes. Typically, this necessitates the use of crutches or a wheelchair, both of which are cumbersome and limit the mobility of the user. Many people in such circumstances opt for a device that allows them to continue walking, such as a boot or other device designed to minimize the impact on the injured area. These devices do not completely relieve the pressure on the injured area, however, potentially prolonging recovery time and increasing the user's pain.

For example, diabetes can cause a variety of injuries to a person's foot, including ulcers. The standard treatment for a foot ulcer is a boot with a pad surrounding the ulcer, with an opening cut into the pad at the location of the ulcer to prevent impact to the ulcer itself. Every step, however, impacts the skin adjacent the ulcer, pulling the healing tissue. This is not only painful, but also delays healing. Unhealed ulcers can lead to amputation. The best course of treatment is to keep any and all pressure from the entire foot, but many people do not want or cannot tolerate the resultant disruption to their lives caused by such lack of mobility.

A further consideration is that a person's knee needs to bend to allow the person to sit or stand without assistance. Many braces, however, are rigid at the knee and do not provide for bending. Getting up from a seated position is very difficult, if not impossible, with a rigid, straight leg brace.

Based on the foregoing, it is desirable to provide a leg support that transfers all of the pressure of walking to the leg rather than the foot.

It is further desirable for such a leg support to allow a user to walk without putting any pressure on the user's foot.

It is further desirable for such a leg support not to touch the bottom of a user's foot at all.

It is further desirable for a user to be able to take such a leg support off and on without having to insert his or her foot through any openings.

It is further desirable for such a leg brace not to inhibit the bending of the user's knee to allow the user to get up from a seated position.

It is further desirable to allow the user to finely adjust the pressure of the leg support to maximize comfort and pressure for all positions: standing, seated, and walking. It is desirable for the user to have total control of the pressure of the leg support on the user's leg. It is further desirable for such a leg brace to allow small adjustments and to hold those adjustments without constant readjustment as the leg support is used.

It is further desirable for such a leg support to have a knee hinge that bends in an arch rather than at a 90° angle, if the leg support extends above the knee.

It is further desirable for the knee hinge of the leg support to bend or flex in only one plane or direction, if the leg support extends above the knee.

It is further desirable for such a leg support to provide confidence in a user to facilitate increased usage.

It is further desirable for such a leg support to be simple and consistent in usage in design, allowing for mass production and affording removal of leg pain and pressure on leg, knee, ankle, foot, and sole of foot without major cost of production.

It is further desirable for such a leg support to allow a user to put the leg support on and take the leg support off easily and to quickly and accurately adjust all pressure and clearance of the sole of the foot.

SUMMARY OF THE INVENTION

In general, in a first aspect, the invention relates to a leg support system for use on a user's leg, the system comprising: an upper assembly, where the upper assembly is conically-shaped and is capable of being secured around the user's leg; and a lower assembly comprising a foot plate and a rigid elongate structure connecting the upper assembly to the foot plate. The upper assembly may comprise a wrap, and may further comprise hook and loop material, such that the hook and loop material is capable of securing the wrap around the user's leg.

The foot plate lies in a plane generally perpendicular to at least a portion of the rigid elongate structure. The rigid elongate structure of the lower assembly may comprise two rigid elongate bars, where the bars are attached to the upper assembly and to the foot plate in such a location that the two bars run along opposing sides of the user's leg during use. The rigid elongate structure of the lower assembly may comprise a hinge assembly allowing an upper portion of the rigid elongate structure and the upper assembly to pivot relative to a lower portion of the rigid elongate structure and the foot plate.

The leg support system may further comprise a first bladder located within the upper assembly, such that inflating the bladder decreases an internal circumference of the upper assembly, and a second bladder located on the bottom of the foot plate, where the second bladder is in fluid communication with the first bladder. When the user takes a step, the second bladder may be compressed between the foot plate and a walking surface, causing air to travel from the second bladder to the first bladder, which may cause the upper assembly to tighten around the user's leg. The leg support system may comprise tubing connecting the first bladder and the second bladder. The tubing may pass through an opening in the foot plate. The leg support system may further comprise a bulb and valve in fluid communication with the first bladder, where the bulb is capable of injecting air into the bladder and the valve is capable of releasing air from the bladder.

The leg support system may further comprise a shoe adaptor. The shoe adaptor may comprise a shoe with a thick sole, or the shoe adaptor may comprise a lift capable of being attached to a sole of a shoe to raise the height of the shoe. The shoe adaptor may have a customizable height. The leg support system may further comprise multiple shoe adaptors of varying heights.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

Figure 7:
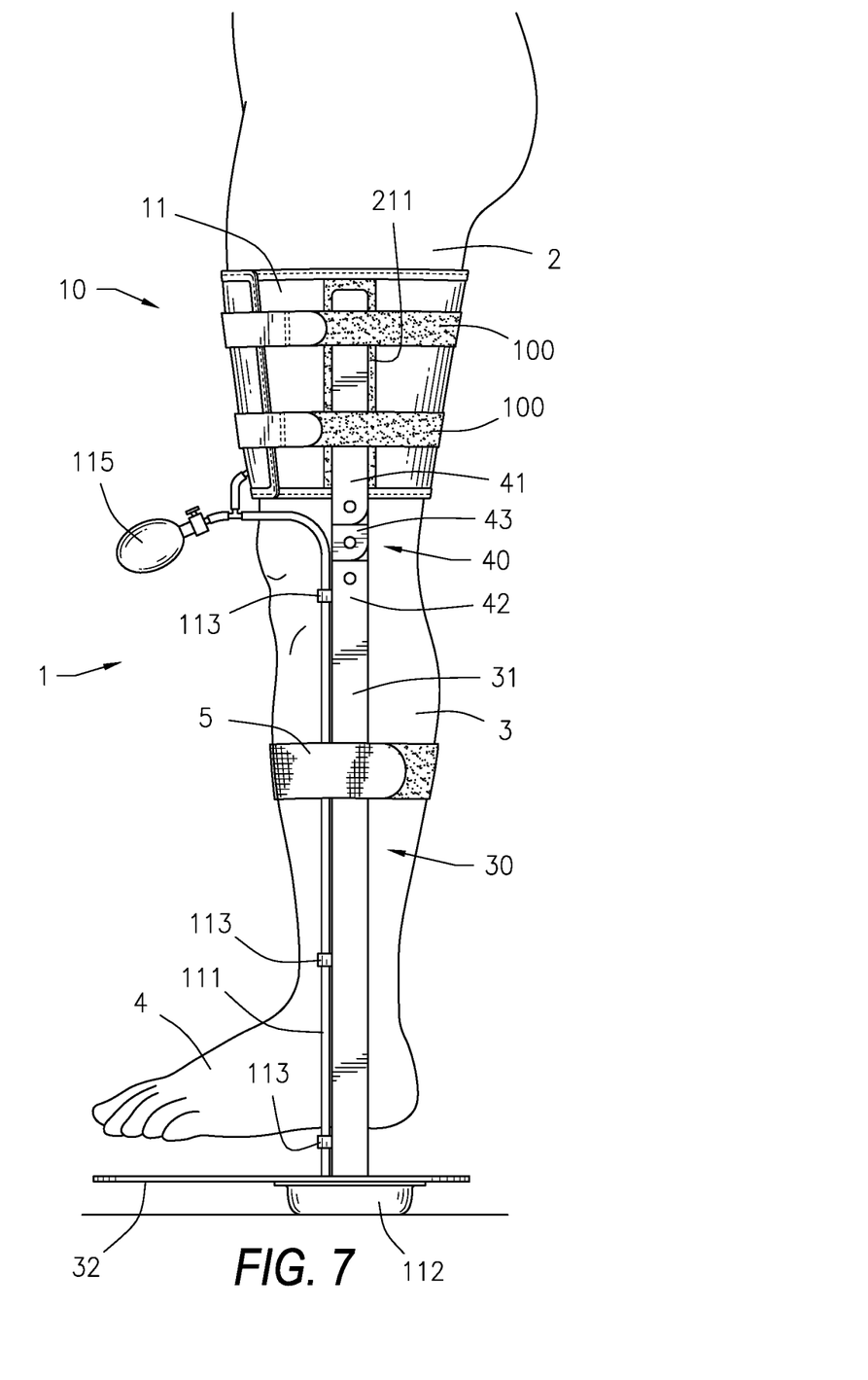
FIG. 7 is a side view of the leg support system in place on the user's upper leg.
Figure 8:
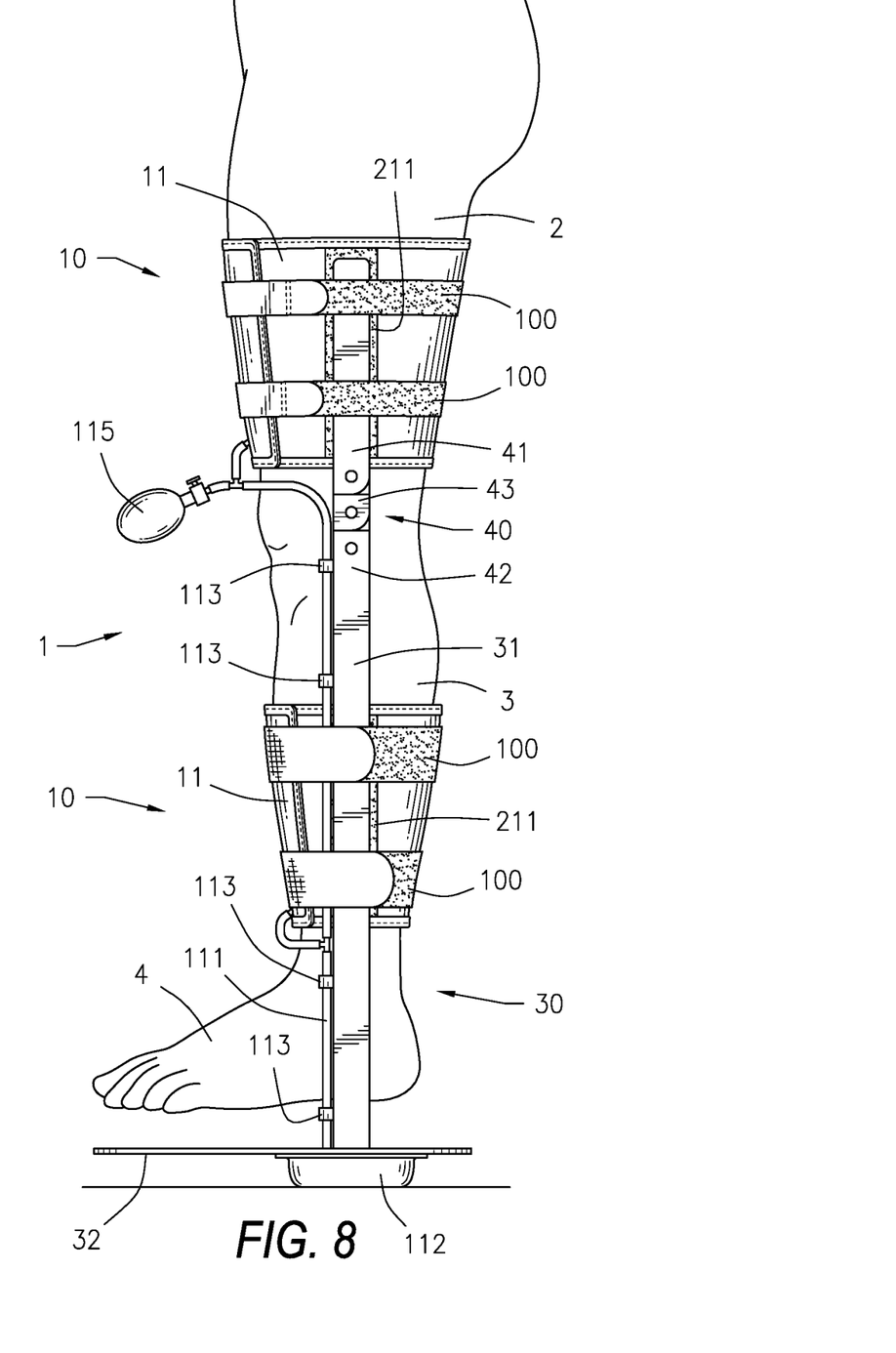
FIG. 8 is a side view of the leg support system with an upper assembly around both the user's upper leg and lower leg.

In general, in a first aspect, the invention relates to a leg support 1. The leg support 1 may wrap around a user's upper leg 2, as shown in FIGS. 7 and 8. The leg support 1 may surround the user's lower leg 3 and foot 4, and may optionally have a strap 5 that secures the leg support 1 to the user's lower leg 3. The strap 5 may allow the user to control their center of gravity within the leg support 1 by moving their lower leg 3 forward or backward in the leg support 1, or the user may use the leg support 1 without the strap if desired. Additionally or alternately, the leg support 1 may wrap around the user's lower leg 3, as shown in FIGS. 1 through 3, 8, and 9, with the leg support 1 surrounding the user's foot 4. Whether the leg support 1 wraps around the user's upper leg 2, lower leg 3, or both the user's upper leg 2 and lower leg 3, the leg support 1 may not touch the user's foot 4, either when the user has his or her weight on his or her leg or not.

The leg support 1 may comprise an upper assembly 10, which surrounds the user's upper leg 2 or lower leg 3 when in use, and a force conveyance assembly 30, which extends from the upper assembly 10 to beyond the user's foot 4 when in use. The force conveyance assembly 30 may be provide passive or active force conveyance.

When the force conveyance assembly 30 provides passive force conveyance, during use, the user may secure the upper assembly 10 around the user's upper leg 2 or lower leg 3 at a comfortable tension. The user may take a step, shifting his or her weight to the leg support 1. As the force conveyance assembly 30 extends beyond the user's foot 4, the force conveyance assembly 30 may come into contact with the floor before the user's foot 4. As a result of coming into contact with the floor, the user's leg may shift downward within the upper assembly 10, which may be conically shaped and thus which may provide increased tension around the leg, as described below, thus essentially causing the user's upper leg 2 or lower leg 3 to bear the user's weight while preventing the user's foot 4 from coming into contact with either the floor or the leg support 1. The result of this unique design may be zero pressure on the sole of the user's foot.

When the force conveyance assembly 30 provides active force conveyance, during use, the user may secure the upper assembly 10 around the user's upper leg 2 or lower leg 3 at a comfortable tension. The user may take a step, shifting his or her weight to the leg support 1. As the force conveyance assembly 30 extends beyond the user's foot 4, the force conveyance assembly 30 may come into contact with the floor before the user's foot 4. As a result of coming into contact with the floor, the force conveyance assembly 30 may cause the upper assembly 10 to tighten around the user's upper leg 2 or lower leg 3, as described below. Thus, a portion of the vertical shear pressure from the step may be transferred into horizontal compressional force around the user's upper leg 2 or lower leg 3, essentially causing the user's upper leg 2 or lower leg 3 to bear the user's weight. The increased compressive force may prevent the upper assembly 10 from slipping on the user's upper leg 2 or lower leg 3 and may keep the user's foot 4 from ever coming into contact with either the floor or the leg support 1. The result of this unique design may be zero pressure on the sole of the user's foot.

Figure 4:
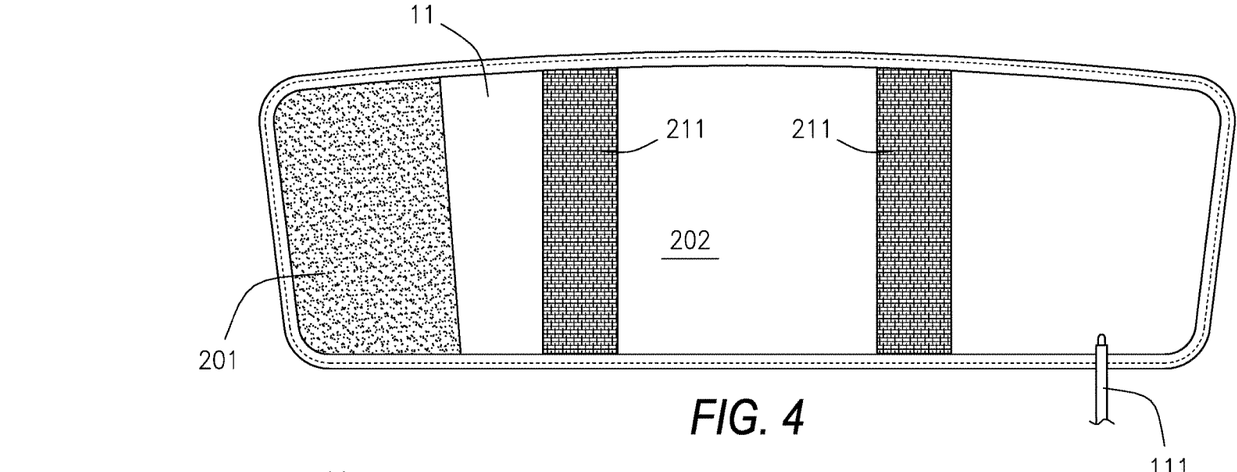
FIG. 4 is a detailed view of the outside upper assembly in an unfolded position.
Figure 5:
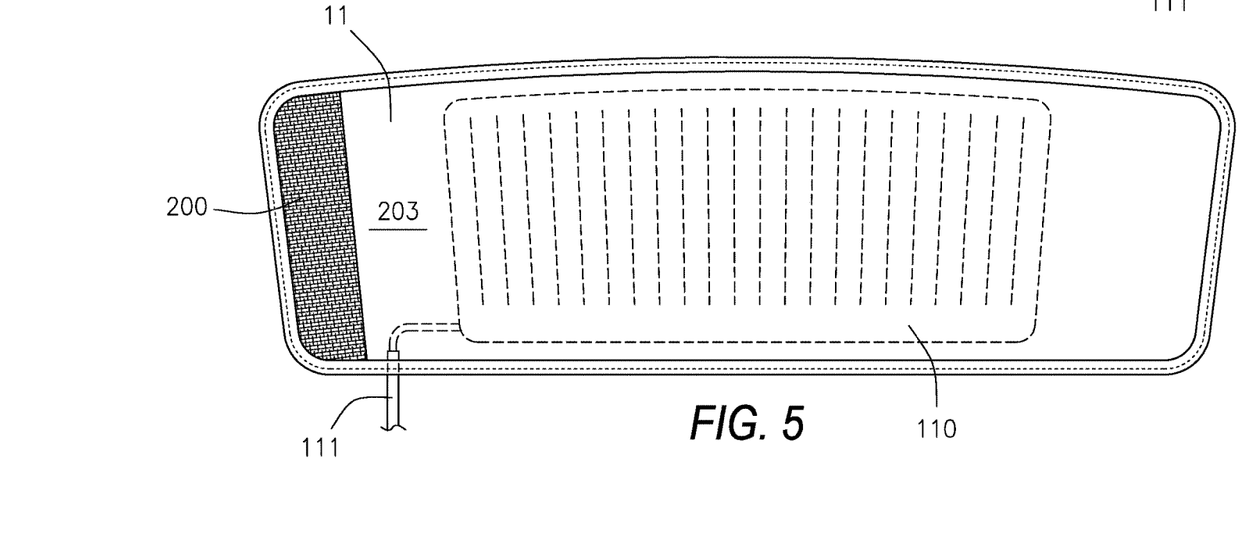
FIG. 5 is a detailed view of the inside of the upper assembly in an unfolded position.

The upper assembly 10 may comprise a wrap 11. The wrap 11 may have a conical shape or may be capable of forming a conical shape. The wrap 11 may have an area of hook material 200 and an area of loop material 201 for securing the wrap 11 to itself in the conical shape, or may be secured by any other desired attachment device or devices. The wrap 11 may be laminated out of two materials: a first layer 202 made of a non-stretchable material, such as ballistic nylon, and a second layer 203 made of a material that grips the user's skin when pressure is applied yet has very little compression, such as leather. The first layer 202 may not distort but may maintain flexible rigidity, allowing the wrap 11 to be bent and wrapped around the user's leg without stretching out in any direction. The first layer 202 may be hard and slick against the user's skin, and thus including the second layer 203 may provide a softer, more comfortable interface against the user's skin. The upper assembly 10 may optionally comprise one or more hook and loop straps 100 for further securing the wrap 11 against the user's upper leg 2 or lower leg 3 and/or to the force conveyance assembly 30, as further described below.

Optionally, the upper assembly 10 may additionally comprise at least one wire encircling at least a portion of the wrap 11. For example, the wires may pass through anchors located on either side of the wrap 11 and around the front of the wrap 11. The anchors may each have two openings through which the wire may pass, one located higher than the other. For example, as shown, one opening may be located above the midline of the upper assembly 10, while the other opening may be located below the midline of the upper assembly 10. By passing through both openings, the wire may provide pressure that is disseminated over a larger area than if the openings were closer together.

The wires may attach to a closure device, allowing the upper assembly 10 to be opened, placed around the user's upper leg 2 or lower leg 3, and closed for use. In particular, both the closure device and the wrap 11 may be opened for placement of the upper assembly 10 around the user's leg 2 or 3, and then both may be closed for use. The closure device may be any desired closure device. The upper assembly 10 may open completely to go around the user's leg and may close completely to allow pressure adjustment. The design of the upper assembly 10 may allow pressure to be totally uniformly distributed around the user's leg with no one pressure point causing pain and discomfort.

The wire may attach to the closure device in such a way that its tension may be adjusted. For example, the closure device may comprise a tensioning device, such that tightening the tensioning device may cause the wire to slide through the anchors, decreasing the amount of wire located between the tensioning device and the anchors, and thus decreasing the diameter of the upper assembly 10. Loosening the tensioning device may produce the opposite effect, assuming the tensioning device was previously tightened such that there is slack wire available. Alternately, multiple wires and multiple tensioning devices may be used.

The upper assembly 10 may further comprise a plate located behind the tensioning device, closure device, and/or wire. The plate may be curved to contour to the user's leg. The plate may be rigid or semi-rigid. The plate may be sufficiently large to cover the all or the majority of the height of the wrap 11, extending from the bottom or near the bottom of the wrap 11 to the top or near the top of the wrap 11. The plate may act to disperse the pressure of the wire across a larger area, increasing the effectiveness of the wire and the comfort of the leg support 1.

The force conveyance assembly 30 may comprise two bars 31 extending downward from the upper assembly 10, where one bar 31 may extend downward from either side of the upper assembly 10. The upper assembly 10 may connect to the force conveyance assembly 30 via an area of either hook or loop material 210 on the upper assembly 10, such as on the outside of the wrap 11, and a corresponding area of either hook or loop material 211 on the force conveyance assembly 30, such as on the inside surface 212 of each of the two bars 31. Additionally or alternately, any other way of or device or devices for attaching the upper assembly 10 to the bars 31 of the force conveyance assembly 30 may be used. The optional hook and loop straps 100 may further secure the force conveyance assembly 30 to the wrap 11 by wrapping around both, compressing the two areas of hood and loop material 210 and 211 against each other via the force of the straps 100 on the one side and the user's leg on the other.

The bars 31 may be joined at their bottoms by a foot plate 32 extending therebetween. The foot plate 32 may be generally rectangular, foot-shaped, or any other desired shape and may be large enough to cover the bottom of the user's foot 4, as shown, or any other desired size. The bars 31 may be sufficiently long that the foot plate 32 is located below, but not touching, the user's foot 4 when the leg support 1 is in use.

If the upper assembly 10 is intended to be worn around the user's upper leg 2, the force conveyance assembly 30 may include further elements to allow the force conveyance assembly 30 to bend at the user's knee 6 for greater ease of use. For example, each of the bars 31 may have a hinge assembly 40. Each bar 31 may comprise an upper bar 41, a lower bar 42, and a middle piece 43 between the upper bar 41 and the lower bar 42. The upper bar 42 may have a rounded corner adjacent the middle piece 43, and the middle piece 43 may have a rounded corner adjacent the lower bar 42. The upper bar 41, middle piece 43, and lower bar 42 may be connected via a connector plate. The upper bar 41, middle piece 43, and lower bar 42 may be pivotally connected to the connector plate via attachment devices, such as screws or bolts. The foregoing elements may allow the bars 31 to bend. The pivot points of the hinge assembly 40 may facilitate the arch bend of the user's knee. The center pivot point may be forward of the other two pivot points to allow the arch movement of middle piece 43 in relation to upper bar 41 and lower bar 42. The eccentric knee bend of the leg support 1 may allow constant pressure in all planes of movement.

Figure 6:
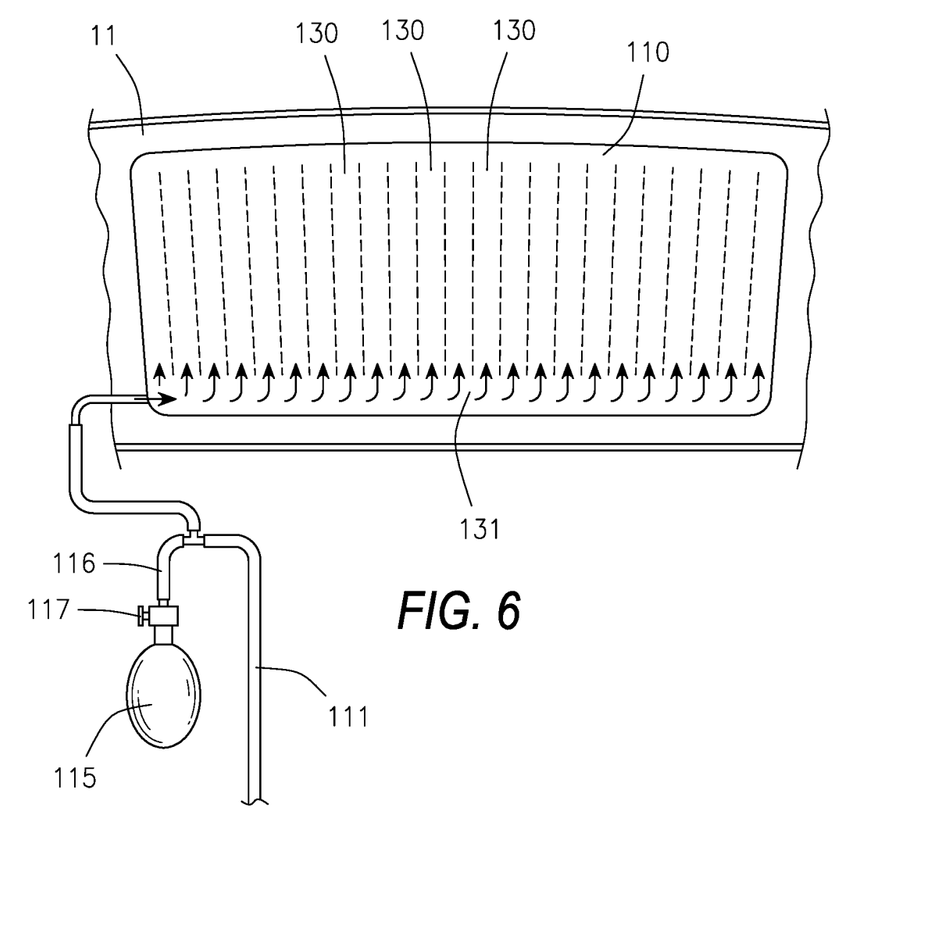
FIG. 6 is a detailed view of the bladder within the upper assembly.

The upper assembly 10 may further comprise a bladder 110. The wrap 11 of the upper assembly 10 may house the bladder 110. The bladder 110 may be large and relatively flat, covering a large surface area within the wrap 11. The bladder 110 may be centered at the back of the wrap 11 and may extend at least halfway around the wrap 11, such that the bladder 110 surrounds at least half of the user's leg when the wrap 11 is in place thereon. The bladder 110 may be attached to and lie against an interior surface of the wrap 11, or may be housed between multiple layers of the wrap 11. Specifically, the bladder 110 may be located between the first layer 202 and the second layer 203, as shown. The material of the second layer 203 may allow just enough stretch to accommodate the inflation of the bladder 110. The bladder 110 may be inflatable, such that inflating the bladder 110 decreases the interior circumference of the upper assembly 10. The large surface area of the bladder 110 may disseminate pressure over a wider area, making the upper assembly 10 more effective and more comfortable to the user.

The bladder 110 may be connected via tubing 111 to a second bladder 112 located on the bottom of the foot plate 32, such that the bladder 110 is in fluid communication with the second bladder 112. The tubing 111 may be a single tube, multiple tubes, one or more connectors, or combinations thereof. The tubing 111 may connect to the bladder 110 at the bottom of the bladder 110, such that air entering the bladder 110 may fill the bottom of the bladder 110 first and may form a seal around the user's leg.

The bladder 110 may have a series of vertical channels 130 extending across its width. The bladder 110 may have an open area 131 below the point at which the vertical channels 130 begin. The tubing 111 may enter the bladder 110 at the open area 131. The open area 131 may have a height bigger than the width of the channels 130. Thus, when air enters he bladder 110, the open area 131 may fill before the channels 130, thus disseminating pressure around the leg rather than making a lump at the back of the leg.

The second bladder 112 may be rounded. In particular, the second bladder 112 may be hemispherical or may define some other dome, spherical or otherwise, with the flat portion lying against the foot plate 32 and the rounded portion pointing downward. The second bladder 112 may be located on the bottom of the foot plate 32 such that the vertex of the second bladder 112 may be located along the user's center of gravity when wearing the leg support 1. This aspect of the leg support 1 may be customizable, with the second bladder 112 being attached to the bottom of the foot plate 32 during fitting of the leg support 1 to a particular user based on the center of gravity of that particular user. For purposes of this placement, the center of gravity of the user may be considered to be the axis at which, when the vertex of the second bladder 112 is located along that axis, the vertex of the second bladder 112 is the first point that comes into contact with the ground or other walking surface when the user takes a step while wearing the leg support 1.

The tubing 111 may be attached to the force conveyance assembly 30 at one or more points, such as through one or more brackets 113 or other devices. The tubing 111 may connect directly to the second bladder 112 or may connect via a connector. The tubing 111, the connector, some portion of the second bladder 112 or some combination thereof may extend through an opening in the foot plate 32. Alternately, the tubing 111, the connector, some portion of the second bladder 112 or some combination thereof may extend around the edge of the foot plate 32.

The bladder 110 may also be in fluid communication with a bulb 115, which may be connected to the bladder 110 via tubing 116 and a valve 117, allowing the user to partially inflate the bladder 110 to a comfortable level prior to use, thus decreasing the amount of air needed from the second bladder 112 to fully inflate the bladder 110. The valve 117 may allow the user to release air from the system. Thus, the user can control the amount of air force in the leg support 1 to a suitable, comfortable, yet effective level.

Figure 3:
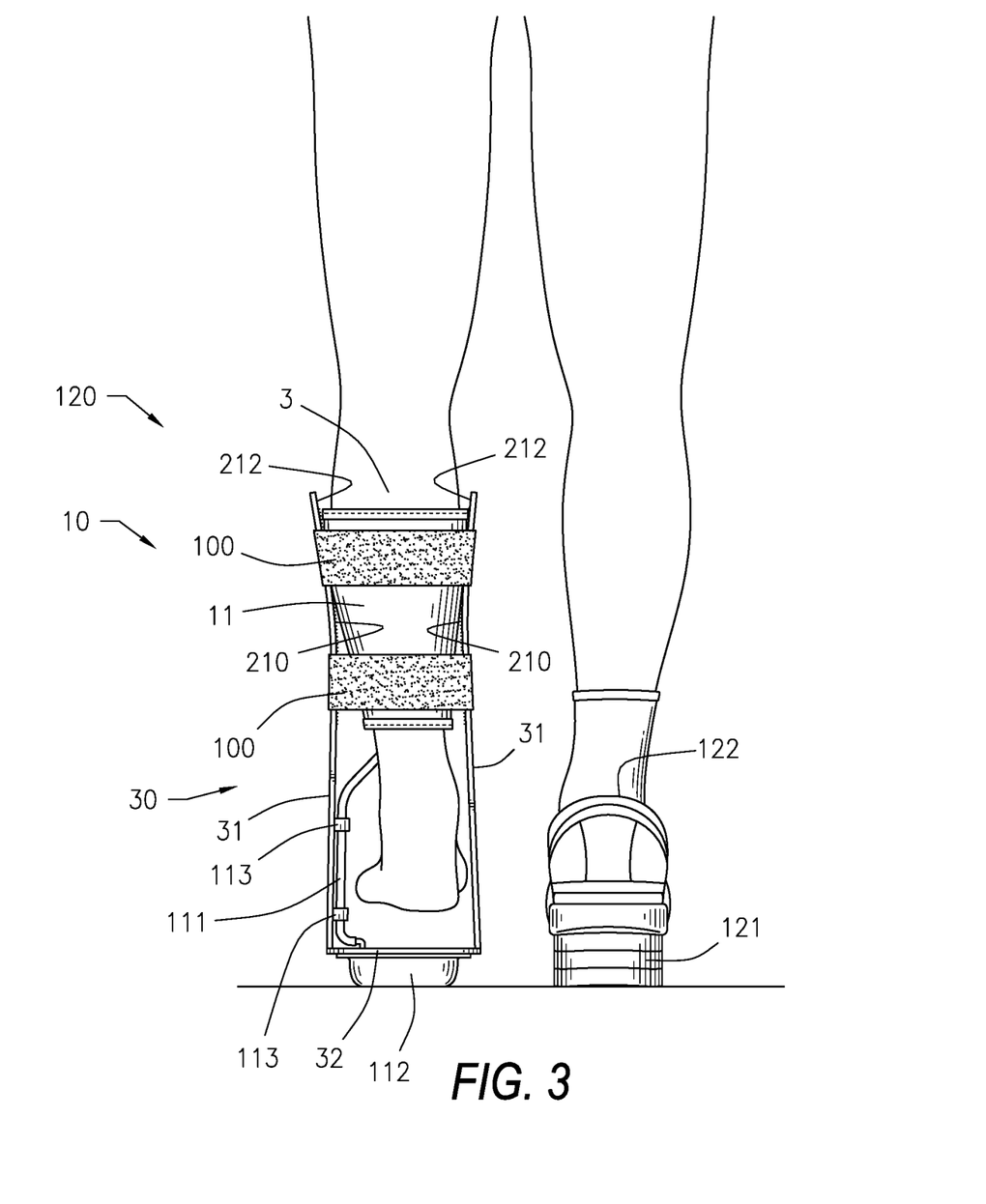
FIG. 3 is a back view of the leg support system in use, with the leg support in the compressed position, also showing a shoe adaptor in place on a shoe on the user's other foot.

The leg support 1 may be part of a leg support system 120 further comprising a shoe adaptor 121. The shoe adaptor 121 may be a shoe with a thick sole or a lift for attaching to an existing shoe. The shoe adaptor 121 may be worn on the user's other foot 122 to bring the height of the user's other foot 122 to the level of the foot 4 on the leg bearing the leg support 1 when the user places his or her weight on the leg bearing the leg support 1. The shoe adaptor 121 may be customizable to a particular user, such that, during fitting of the leg support 1 to a particular user, the height of the shoe adaptor 121 may be adjusted to ensure that both of the user's feet 4 and 122 are at the same height and the user's pelvis is level when the user is wearing the leg support 1 and the shoe adaptor 121. The leg support system 120 may comprise a plurality of shoe adaptors 121, facilitating the customized fit of the leg support system 120 to a particular user.

During use, the user may open the upper assembly 10, if not already open, place his or her leg therein, and close the upper assembly 10. Opening the upper assembly 10 may comprise opening the closure device, if present, opening the hook and loop material 200 and 201, if present, and opening the wrap 11. Closing the upper assembly 10 may comprise closing the wrap 11 around the user's leg, with the bladder 110, if present, located at the back of the user's leg, securing the hook and loop material 200 and 201, if present, and closing the closure device 17, if present. The user may close the hook and loop material 200 and 201, if present, tight enough that the wrap 11 is secure against the user's leg but not uncomfortably tight.

The user may place the upper assembly 10 between the bars 31 of the force conveyance assembly 30, securing the hook and loop material 210 and 211, if present, or may otherwise attach the upper assembly 10 to the bars 31 of the force conveyance assembly 30. Straps 100, if present, may be secured therearound. The user may ensure that his or her foot 4 is not in contact with the foot plate 32 prior to securing the upper assembly 10 to the force conveyance assembly 30.

The user may then tighten the tensioning device, if present, to more precisely and securely secure the wrap 11 against the user's leg, but again not uncomfortably tight. The user may then squeeze the bulb 115 to inject air into the bladder 110, if present and if needed. These actions, namely tightening the hook and loop material 100 if present, tightening the tension device if present, and injecting air into the bladder 110 if present via the bulb 115 or other device, may allow the user to finely calibrate the tightness of the upper assembly 10 to be as tight as possible without being uncomfortable. They may also allow the user to ensure that this tightness is not lost during use of the leg support 1 due to stretching or relaxing of the components thereof.

Figure 1:
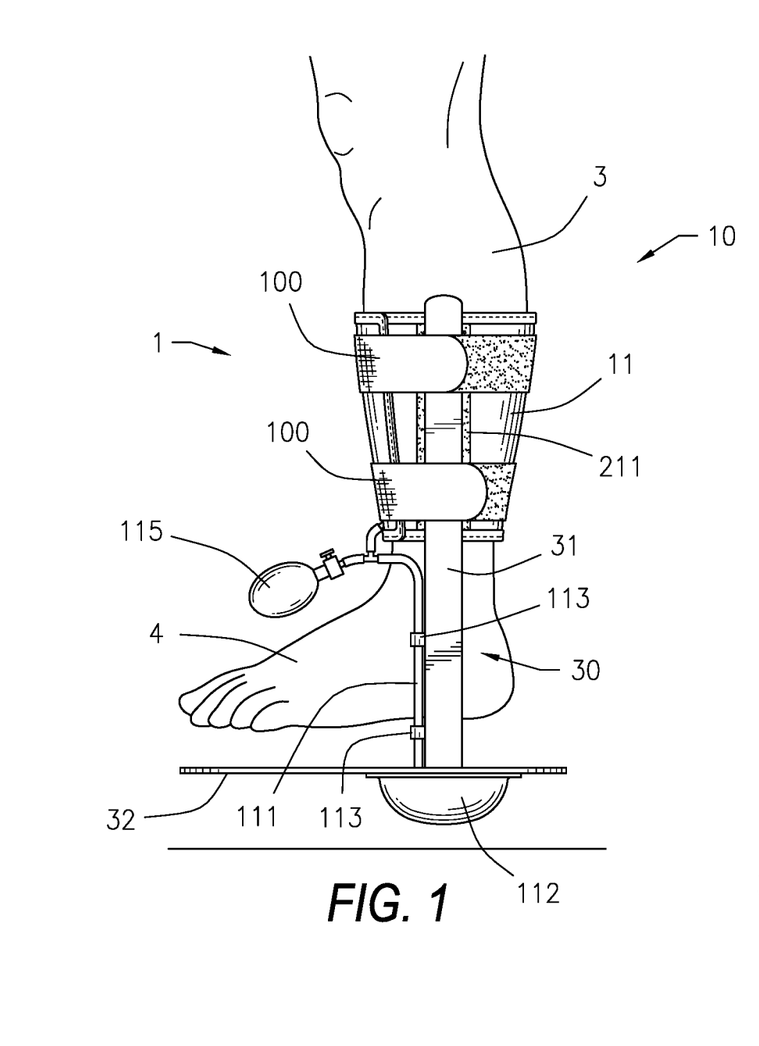
FIG. 1 is a side view of the leg support system of the present invention in place on a user's lower leg, with the leg support in a relaxed position.
Figure 2:
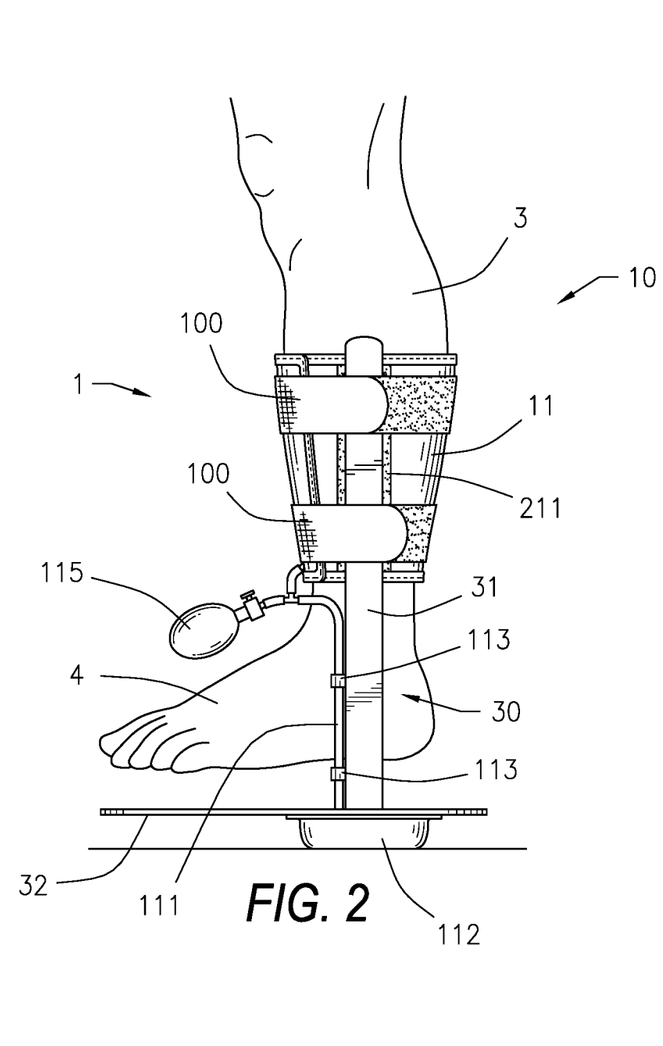
FIG. 2 is a side view of the leg support system in place on a user's leg, with the leg support in a compressed position.

If the leg support 1 has the air bladder system, while wearing the shoe adaptor 121, if present, on the user's other foot, the user may take a step onto the leg bearing the leg support 1. The second bladder 112 may come into contact with the ground or other walking surface and may be compressed against it. As the second bladder 112 is compressed, air within the second bladder 112 may travel up the tubing 111 to the bladder 110 in the upper assembly 10. The addition of air into the bladder 110 may decrease the interior circumference of the upper assembly 10, tightening the upper assembly 10 around the user's leg to the point that the user's leg cannot slide downward within the upper assembly and the user's foot 4 cannot come into contact with the foot plate 32. Rather, the user's weight may be borne entirely by the leg support 1 and the user's upper leg 2 or lower leg 3, depending on where the leg support 1 is secured, with no pressure on the user's foot 4.

When the user takes a step with the other foot 122, taking his or her weight off of the leg support 1, air may return from the bladder 110 to the second bladder 112. This may allow the upper assembly 10 to return to a comfortable tightness around the user's leg. The process may repeat with each step.

Figure 9:
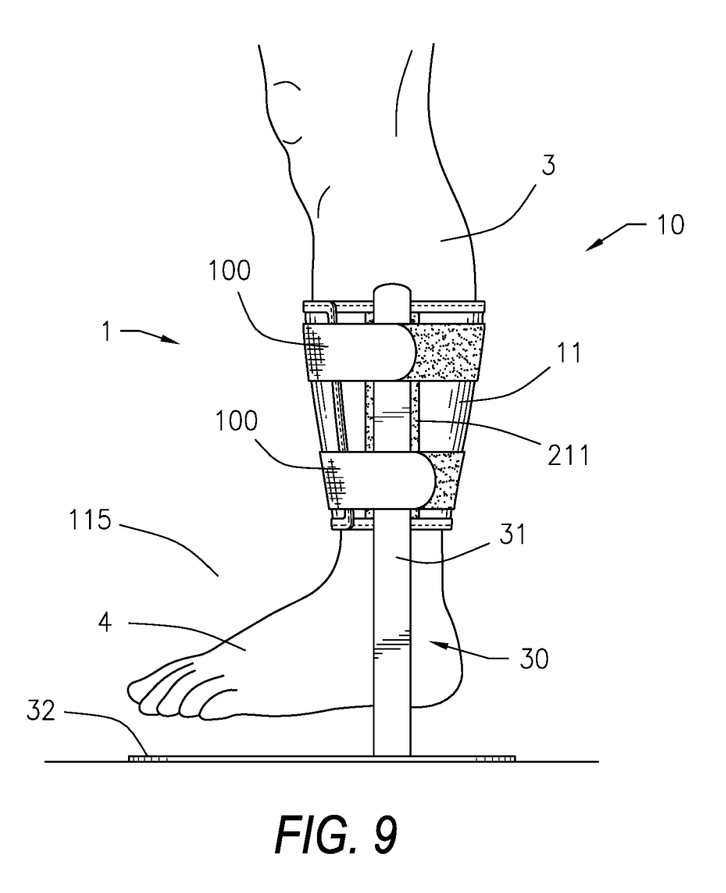
FIG. 9 is a side view of the leg support system without the bladder option.

Alternately, if the leg support 1 does not have the air bladder system, when the user takes a step onto the leg bearing the leg support 1, the foot plate 32 may come into contact with the ground or other walking surface. The user's leg, being conically shaped at the point where the wrap 11 is placed, may not be able to slide through the wrap 11, being also conically shaped and non-distortable. Thus, the user's foot 4 may not be able to come into contact with the foot plate 32. Rather, the user's weight may be borne entirely by the leg support 1 and the user's upper leg 2 or lower leg 3, depending on where the leg support 1 is secured, with no pressure on the user's foot 4.

Whereas, the devices and methods have been described in relation to the drawings and claims, it should be understood that other and further modifications, apart from those shown or suggested herein, may be made within the spirit and scope of this invention.

What is claimed is:

1. A leg support system for use on a user's leg and foot, the system comprising: an upper assembly, where the upper assembly is capable of being secured around the user's leg at a distance from the user's foot; a lower assembly comprising: a foot plate; and a rigid elongate structure connecting the upper assembly to the foot plate, where the rigid elongate structure has a length configured to be greater than the distance to the user's foot such that the user's foot does not touch the foot plate; a first bladder located within the upper assembly such that inflating the bladder decreases an internal circumference of the upper assembly; and a second bladder located on a bottom of the foot plate, where the second bladder is in fluid communication with the first bladder; such that, when the user takes a step, the second bladder is compressed between the foot plate and a walking surface, causing air to travel from the second bladder to the first bladder, which causes the upper assembly to tighten around the user's leg, preventing the user's foot from striking the walking surface or any part of the leg support system.

2. The leg support system of claim 1 where the upper assembly comprises a wrap.

3. The leg support system of claim 2 where the upper assembly further comprises hook and loop material, such that the hook and loop material is capable of securing the wrap around the user's leg.

4. The leg support system of claim 1 further comprising tubing connecting the first bladder and the second bladder.

5. The leg support system of claim 4 where the tubing passes through an opening in the foot plate.

6. The leg support system of claim 1 further comprising a shoe adaptor.

7. The leg support system of claim 6 where the shoe adaptor comprises a shoe with a thick sole.

8. The leg support system of claim 6 where the shoe adaptor comprises a lift capable of being attached to a sole of a shoe with a height to raise the height of the shoe.

9. The leg support system of claim 6 where the shoe adaptor has a customizable height.

10. The leg support system of claim 6 further comprising multiple shoe adaptors of varying heights.

11. The leg support system of claim 1 where the foot plate lies in a plane generally perpendicular to at least a portion of the rigid elongate structure.

12. The leg support system of claim 1 where the rigid elongate structure of the lower assembly comprises two rigid elongate bars, where the bars are attached to the upper assembly and to the foot plate in such a location that the two bars are configured to run along opposing sides of the user's leg during use.

13. The leg support system of claim 1 where the rigid elongate structure of the lower assembly comprises a hinge assembly allowing an upper portion of the rigid elongate structure and the upper assembly to pivot relative to a lower portion of the rigid elongate structure and the foot plate.

14. The leg support system of claim 1, further comprising a bulb and valve in fluid communication with the first bladder, where the bulb is capable of injecting air into the first bladder and the valve is capable of releasing air from the first bladder.

* * * * *